United States Patent
Giger et al.

(10) Patent No.: US 8,298,240 B2
(45) Date of Patent: Oct. 30, 2012

(54) REMOTELY ADJUSTABLE TISSUE DISPLACEMENT DEVICE

(75) Inventors: Lukas Giger, Basel (CH); Hans Flueckiger, Oetwil am See (CH); Hugo Flueckiger, Derendingen (CH)

(73) Assignee: Synthes (USA), West Chester, PA (US)

( * ) Notice: Subject to any disclaimer, the term of this patent is extended or adjusted under 35 U.S.C. 154(b) by 1573 days.

(21) Appl. No.: 11/697,110

(22) Filed: Apr. 5, 2007

(65) Prior Publication Data

US 2007/0239161 A1 Oct. 11, 2007

Related U.S. Application Data

(60) Provisional application No. 60/790,589, filed on Apr. 6, 2006, provisional application No. 60/866,739, filed on Nov. 21, 2006.

(51) Int. Cl.
*A61B 17/60* (2006.01)
(52) U.S. Cl. ......................................................... 606/90
(58) Field of Classification Search .................... 606/60, 606/250, 258–260, 280, 90, 902–906
See application file for complete search history.

(56) References Cited

U.S. PATENT DOCUMENTS

| | | | | |
|---|---|---|---|---|
| 3,976,060 | A | 8/1976 | Hildebrandt et al. | 128/84 |
| 4,615,338 | A | 10/1986 | Ilizarov et al. | 128/92 |
| 5,626,579 | A | 5/1997 | Muschler et al. | 606/60 |
| 5,720,746 | A | 2/1998 | Soubeiran | 606/61 |
| 6,796,984 | B2 | 9/2004 | Soubeiran | 606/61 |
| 6,972,020 | B1* | 12/2005 | Grayson et al. | 606/90 |
| 7,011,658 | B2* | 3/2006 | Young | 606/258 |
| 2002/0156480 | A1* | 10/2002 | Overes et al. | 606/90 |
| 2002/0161374 | A1 | 10/2002 | Cohen et al. | 606/90 |
| 2005/0234448 | A1 | 10/2005 | McCarthy | 606/57 |
| 2005/0245928 | A1* | 11/2005 | Colleran et al. | 606/61 |
| 2005/0246034 | A1 | 11/2005 | Soubeiran | 623/23.45 |
| 2006/0036259 | A1* | 2/2006 | Carl et al. | 606/90 |

FOREIGN PATENT DOCUMENTS

| | | |
|---|---|---|
| FR | 2834200 | 7/2007 |
| JP | 9056736 | 3/1997 |
| SU | 865284 | 9/1981 |
| WO | WO 99/51160 | 10/1999 |
| WO | WO 02/056777 | 7/2002 |
| WO | WO 02/071962 | 9/2002 |
| WO | WO 2004/058083 | 7/2004 |
| WO | WO 2007/144489 | 12/2007 |

OTHER PUBLICATIONS

VEPTR, Vertical Expandable Prosthetic Titanium Rib Technique Guide, May 2007.
Office Action dated Oct. 18, 2010, issued in the State Intellectual Property Office, P.R. for Application No. 200780021107.2.
International Search Report for WO 2007/118177 dated Oct. 18, 2007.

* cited by examiner

*Primary Examiner* — Kevin T Truong
*Assistant Examiner* — Michael Araj
(74) *Attorney, Agent, or Firm* — McKeon, Meunier, Carlin & Curfman, LLC

(57) ABSTRACT

The invention relates to an apparatus for displacing tissue within the body, wherein the apparatus includes two or more attachment members selectively displaceable with respect to each other via a driving member. The driving member preferably is rotatable and is caused to rotate by manually activating an actuator by applying a depressing force from outside the body.

28 Claims, 13 Drawing Sheets

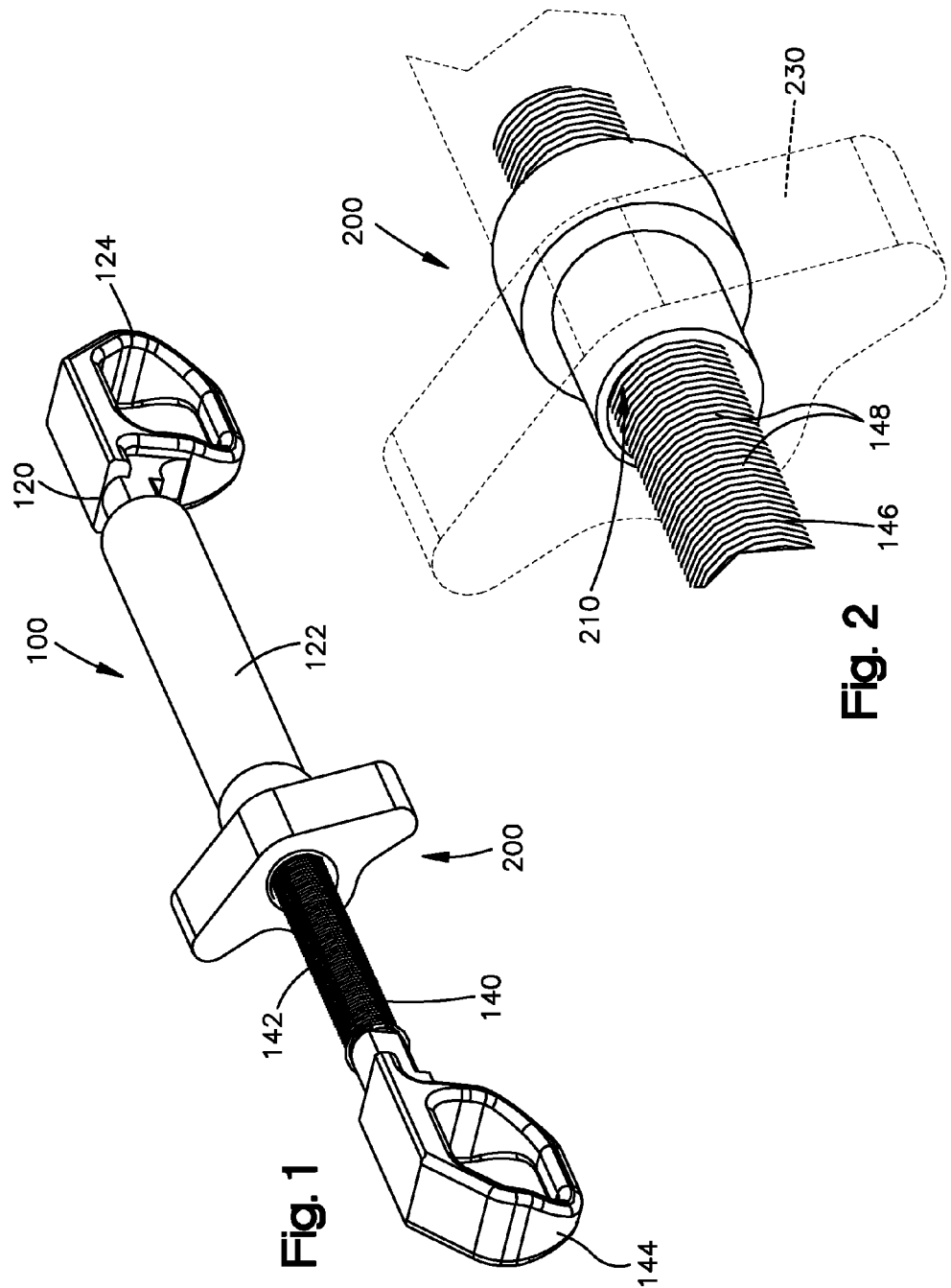

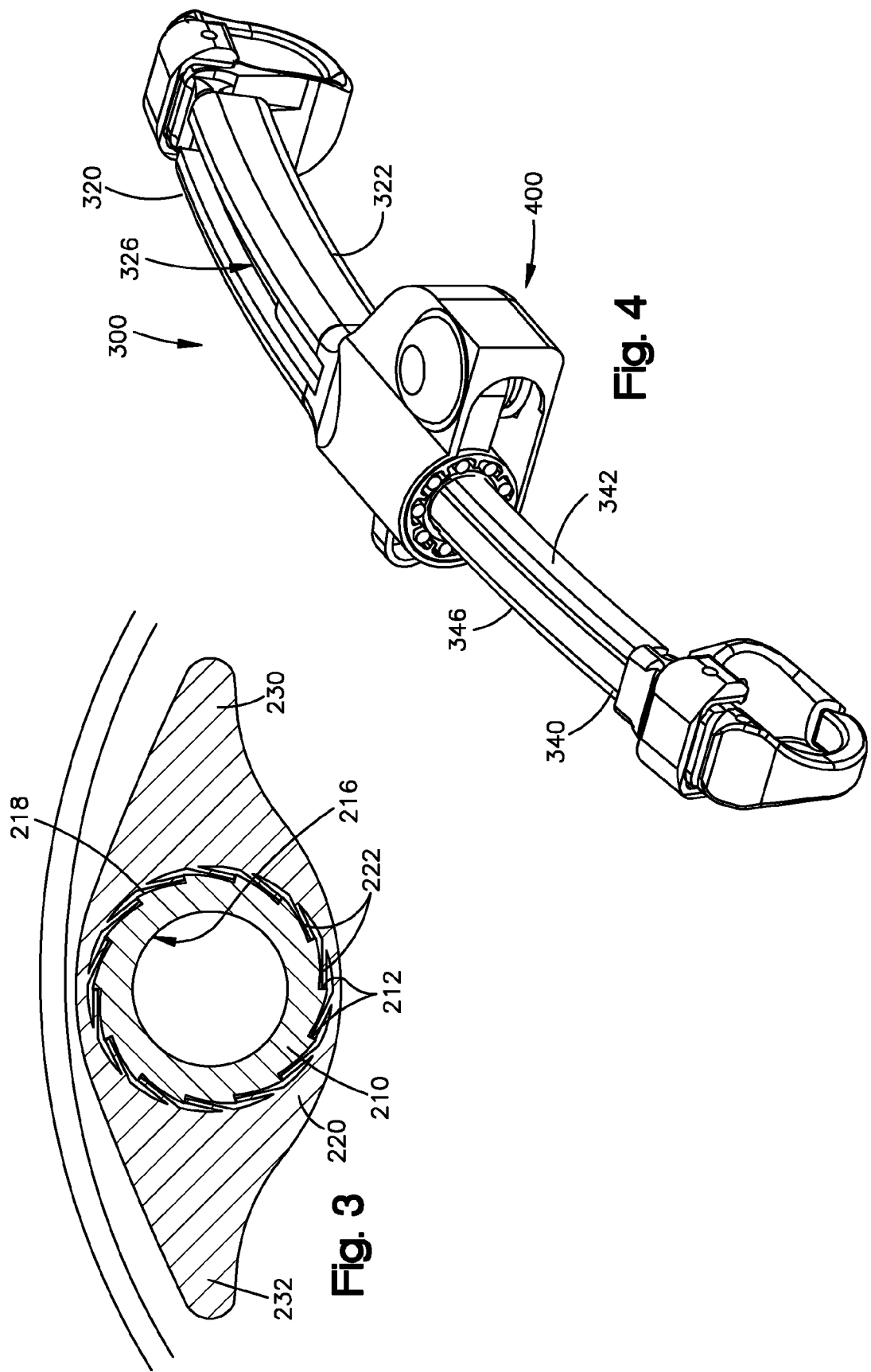

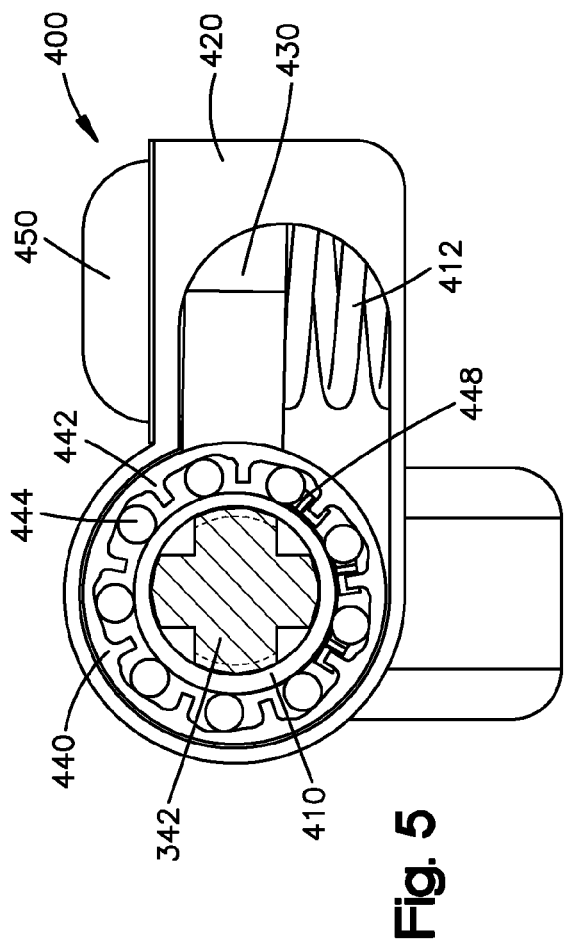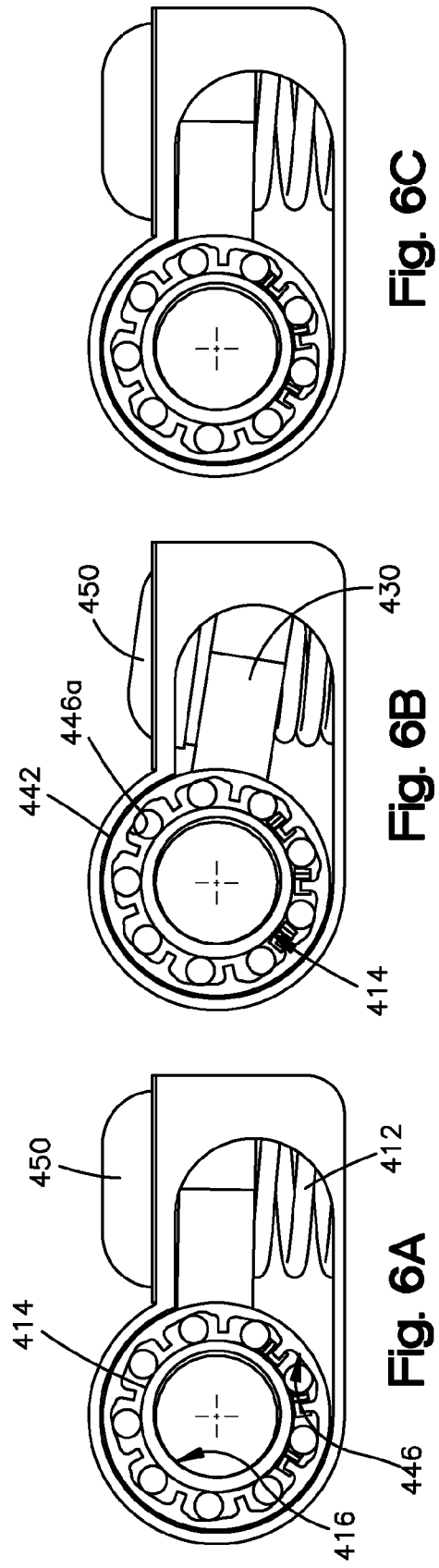
Fig. 5
Fig. 6A
Fig. 6B
Fig. 6C

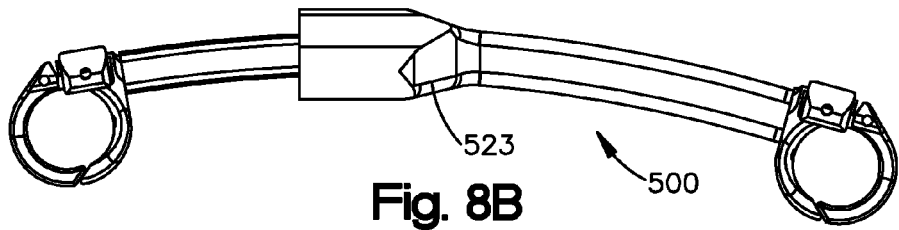
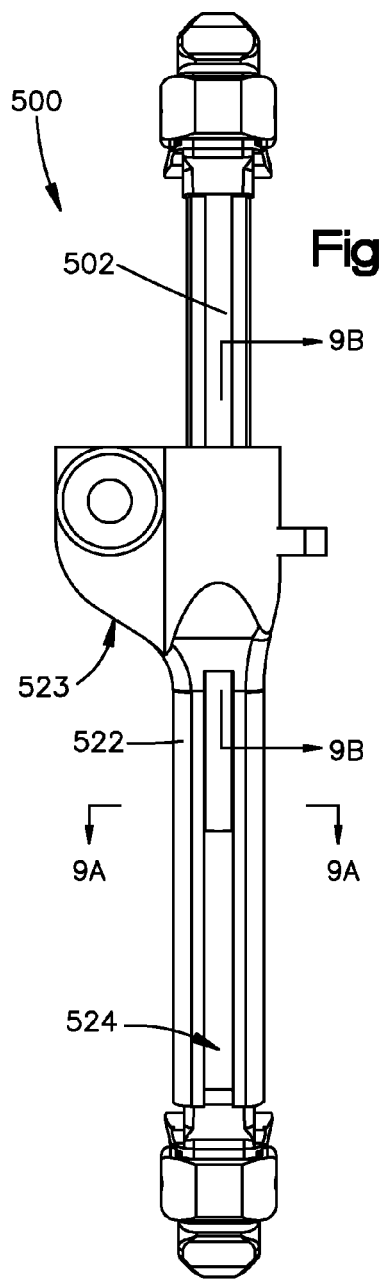
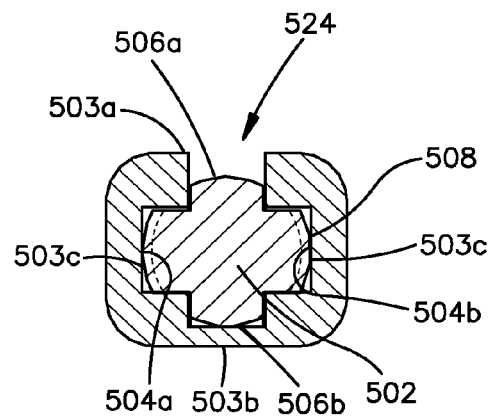
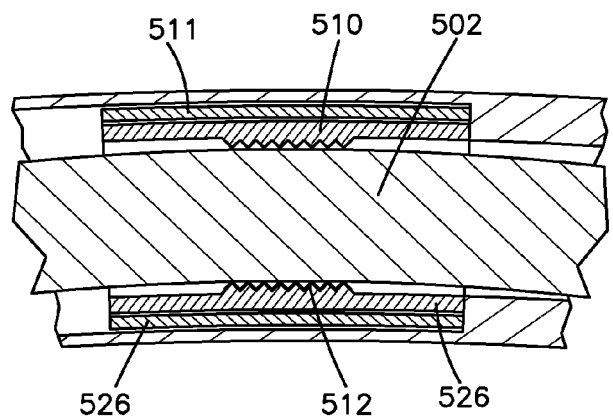

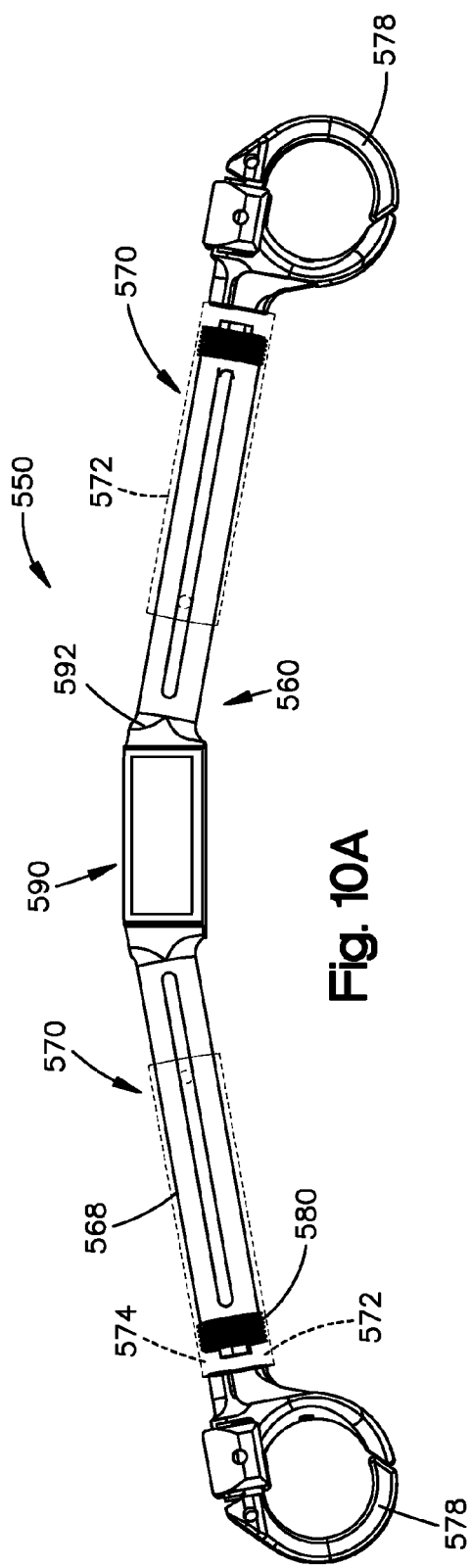
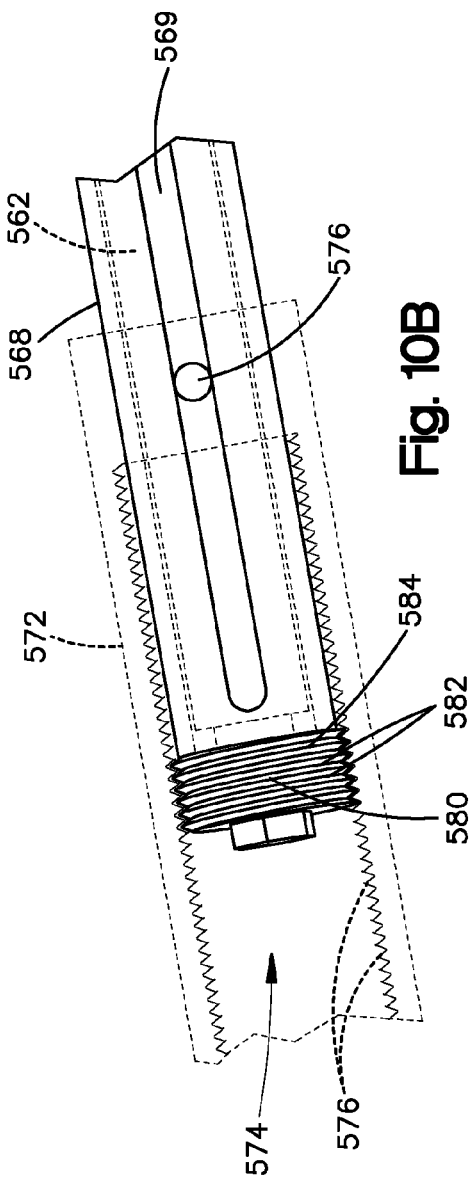
Fig. 10A
Fig. 10B

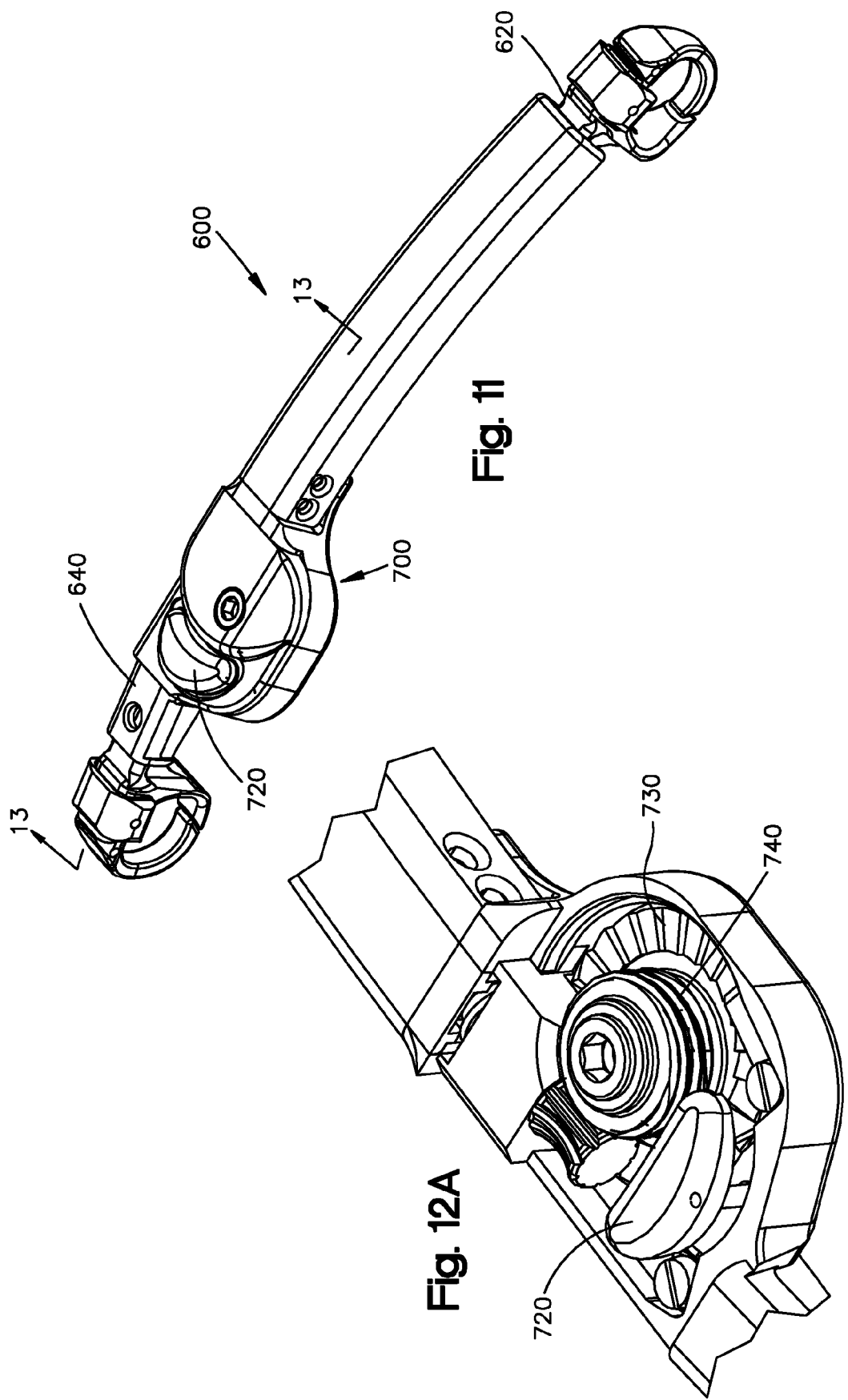

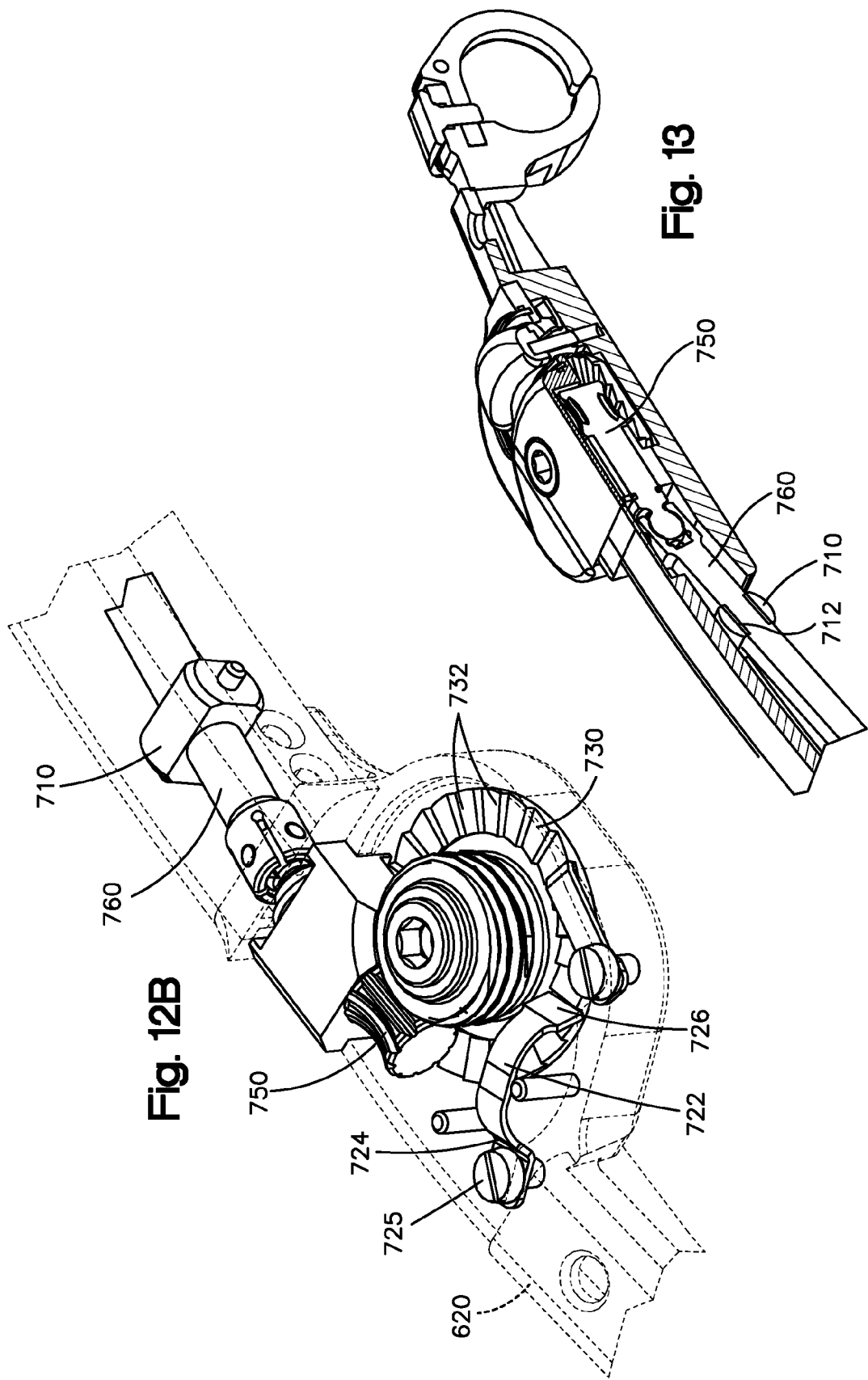

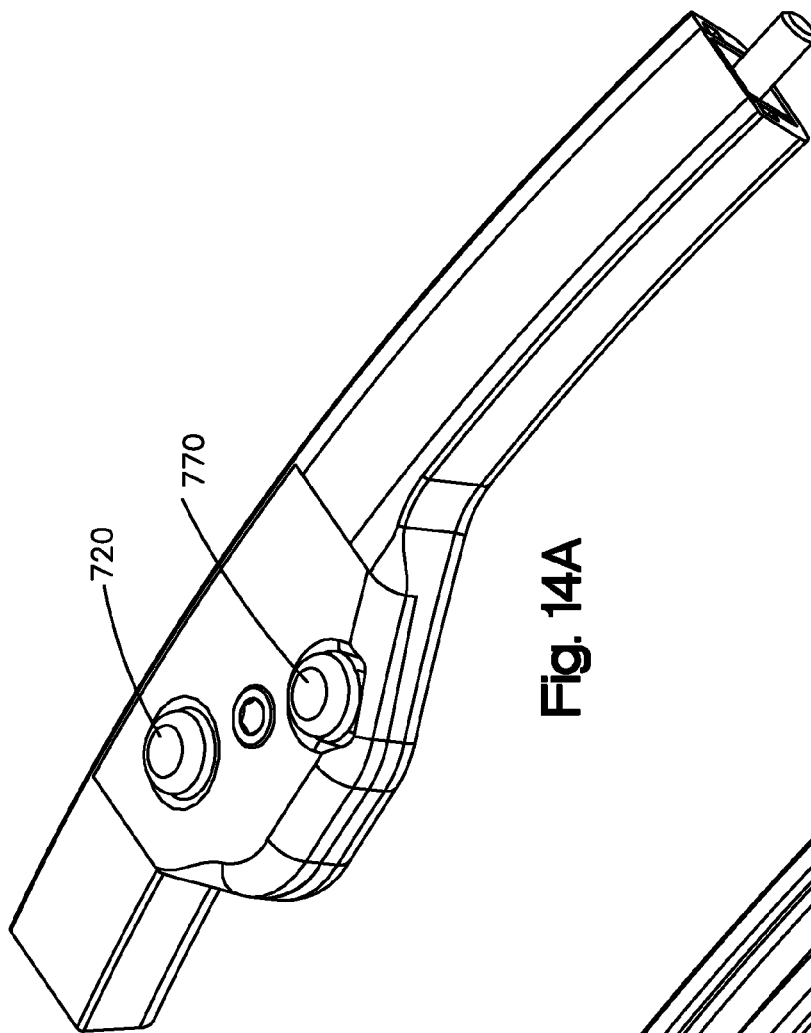
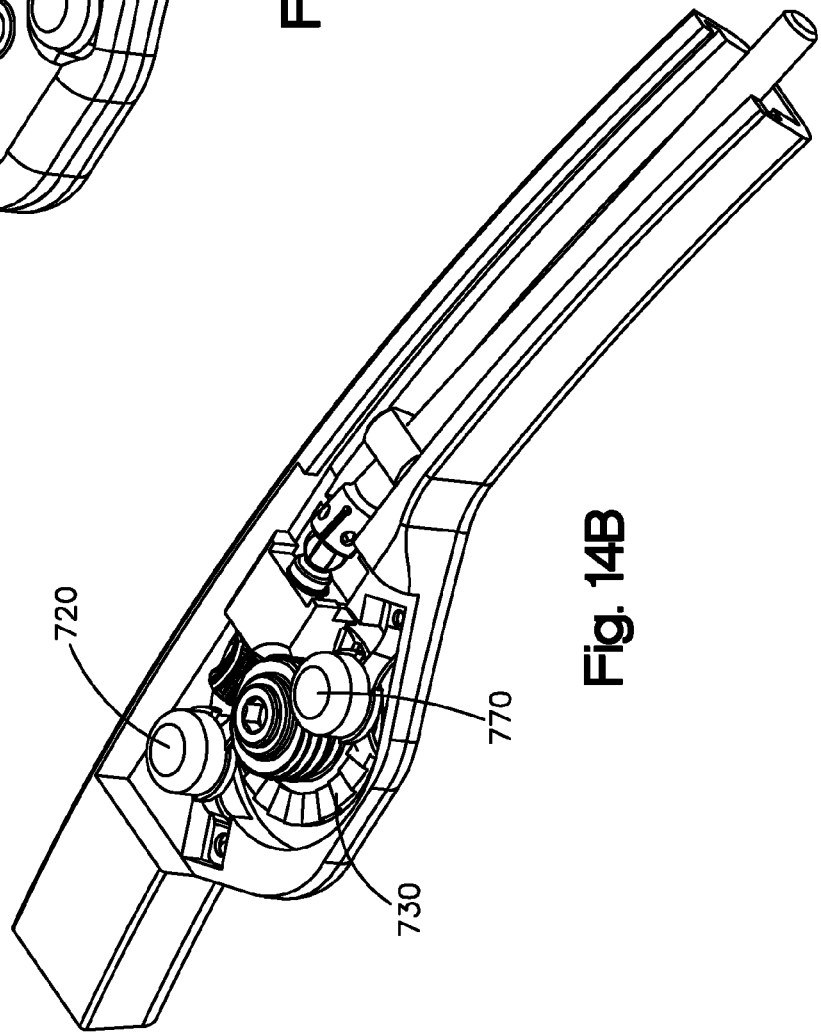

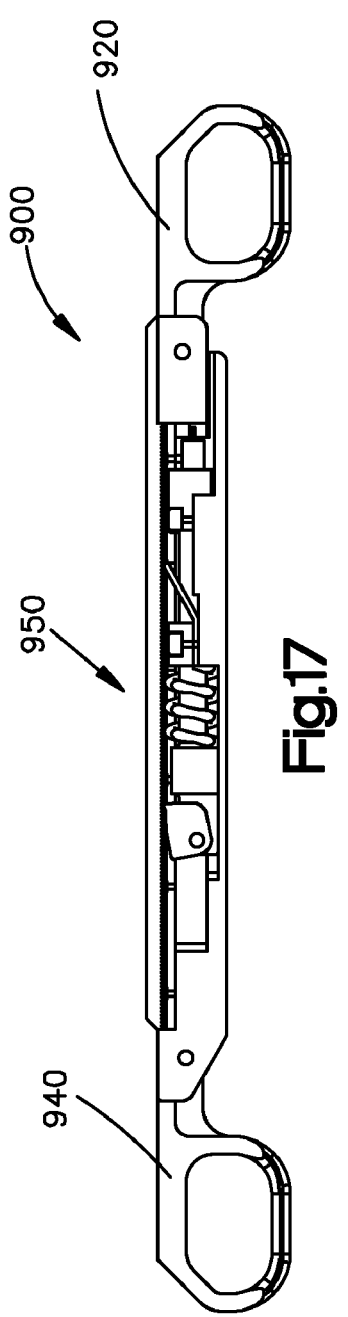
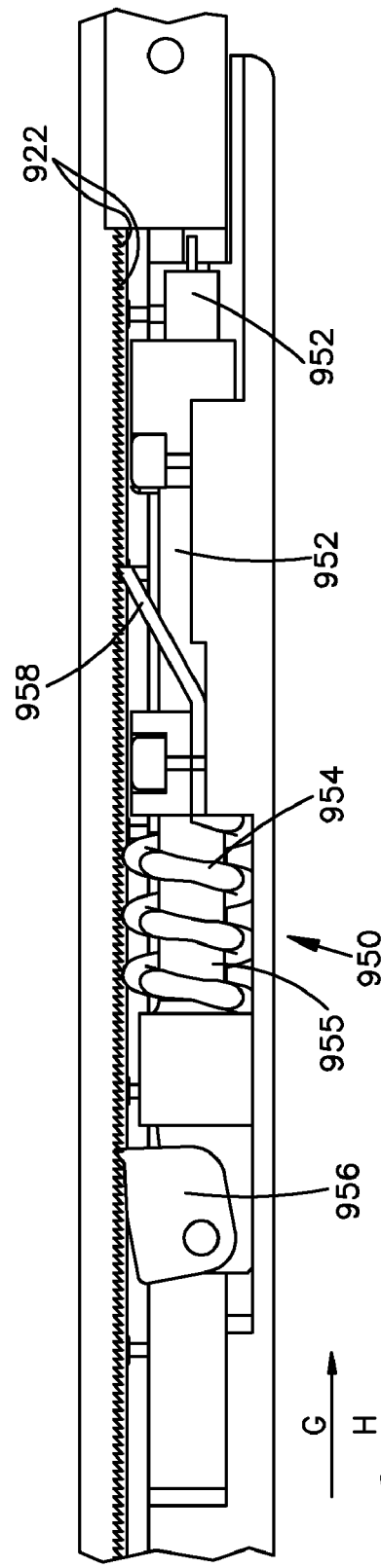

REMOTELY ADJUSTABLE TISSUE DISPLACEMENT DEVICE

CROSS-REFERENCE TO RELATED APPLICATIONS

This application claims the benefit of U.S. Provisional Application Ser. No. 60/790,589 filed on Apr. 6, 2006, entitled "REMOTELY ADJUSTABLE EXPANDABLE DEVICE" and U.S. Provisional Application Ser. No. 60/866,739 filed on Nov. 11, 2006, entitled "REMOTELY ADJUSTABLE BONE DISPLACEMENT DEVICE", both of which are hereby incorporated in their entirety by reference.

TECHNICAL FIELD OF THE INVENTION

The invention generally relates to a device for displacing tissue within a body, such as one or more bones of an animal. More specifically, the invention relates to implants within a patient that can be remotely adjusted from outside the body to extend and/or contract.

BACKGROUND OF THE INVENTION

Expandable implants such as the system commercially available by Synthes, Inc. under the trademark VEPTR® (Vertically Expandable Prosthetic Titanium Rib) system are used to displace bones within a patient. For example, small children with heavy spinothoracic deformities often use such implants attached to the ribs, spine and/or pelvis. The implant is adjusted, usually at regular intervals such as every 6 months, through small skin incisions. However, the adjustment often requires general anesthesia and hospital stay to recover from the adjustment procedure, and also introduces a risk of infection.

SUMMARY OF THE INVENTION

Generally speaking, a device for moving tissue, such as an implant for displacing bone is provided. The device may include two elongated members each having a proximal end and a distal end, and a movement mechanism connected to one of the elongated members and configured to create a rotary motion to move the elongated members relative to each other, wherein the movement mechanism is capable of being activated to create the rotary motion by a user from outside the patient's body.

In accordance with one embodiment of the device, the device may include a first elongated member having a threaded portion and a second elongated member operably associated with a driving member, the driving member having a threaded portion constructed and arranged to engage the threaded portion of the first elongated member. The device may also include a displacement mechanism and a clutch mechanism associated with the displacement mechanism and the driving member. Preferably, the clutch mechanism includes a first condition wherein upon rotation of the displacement mechanism in a first direction, the driving member rotates in the first direction. The clutch mechanism preferably has a second condition wherein upon rotation of the displacement mechanism in a second direction different from the first direction, the driving member remains stationary without rotating.

Another embodiment of the device can include a first attachment member, a second attachment member and a movement mechanism. The movement mechanism may include a rotating member having a plurality of teeth, at least one deflectable member having a contact end for contacting at least one of the plurality of teeth, and a screw member operably associated with the rotating member such that the screw member rotates as the rotating member rotates. Preferably, the movement mechanism also includes a spindle having a first threaded portion and a worm gear operably associated with the screw member. The spindle and the worm gear are preferably connectable. Additionally, the movement mechanism may include a driving member operatively associated with the spindle, wherein the driving member has a second threaded portion constructed and arranged to engage the first threaded portion of the spindle. Furthermore, the driving member is preferably operatively associated with the second attachment member such that movement of the spindle relative to the driving member results in the displacement of the second attachment member relative to the first attachment member.

A further embodiment of the device includes a first attachment member, a second attachment member and a driven member coupled to the first bone attachment member. The device may also include a rotatable driving member coupled to the second bone attachment member, and further include screw threads engaged between the driving member and the driven member to move the driven member axially relative to the second bone attachment member for displacement of the bone attachment members upon rotation of the driving member in a displacement direction. Preferably, the device may also include a manually rotatable actuator and a clutch mechanism operative between the actuator and the driving member to advance the driving member in the displacement direction upon rotation of the actuator back and forth in opposite directions. Moreover, the clutch is preferably interposed radially between the actuator and the driving member in a position axially overlying the screw threads positioned between the driving member and the driven member.

Yet another embodiment of the device may include a first bone attachment member, a second bone attachment member having a driving member, an actuator and a clutch mechanism operatively associated with the driving member to advance the driving member in a displacement direction. The clutch mechanism preferably includes a plurality of rollers and a housing containing the rollers and the driving member, the housing having a converging inner wall portion. Preferably, the clutch mechanism has a first condition wherein upon rotation of the housing in a first direction, the rollers are wedged between the housing and the driving member, and the driving member rotates in the first direction. The clutch mechanism may also have a second condition wherein upon rotation of the housing in a second direction different from the first direction, the driving member remains stationary without rotating. Preferably, the actuator includes a displaceable lever constructed and arranged to rotate the housing in the first direction upon displacement of the lever in a first displacement direction, and in the second direction upon displacement of the lever in a second displacement direction.

One object of the device is to provide a remotely adjustable implant for displacing tissue within a patient's body.

The device may comprise the features of construction, combination of elements, and arrangement of parts which will be exemplified in the construction hereinafter set forth, but the scope of the invention should not be limited to such features, combination of elements or arrangement of parts.

The invention accordingly comprises the several elements and the relation of one or more of such elements with respect to each of the others, and the apparatus embodying features of construction, combination (s) of elements and arrangement of parts which are adapted to effect such steps, all as exemplified in the following detailed disclosure, and the scope of the invention will be indicated in the claims.

BRIEF DESCRIPTION OF THE INVENTION

For a fuller understanding of the invention, reference is had to the following description, taken in connection with the accompanying drawings, in which:

FIG. 1 is a perspective view of an embodiment of a device;

FIG. 2 is a perspective view of an embodiment of a drive assembly;

FIG. 3 is a side elevational view of an embodiment of a drive assembly;

FIG. 4 is a perspective view of an embodiment of a device;

FIG. 5 is a side elevational view of an embodiment of a drive assembly having an embodiment of a clutch mechanism;

FIG. 6A is a side elevational view of the drive assembly of FIG. 5 wherein the clutch mechanism is in a first position;

FIG. 6B is a side elevational view of the drive assembly of FIG. 5 wherein the clutch mechanism is in a second position;

FIG. 6C is a side elevational view of the drive assembly of FIG. 5 wherein the clutch mechanism is in a third position;

FIG. 8A is a top planar view of an embodiment of a device;

FIG. 8B is a front elevational view of the device of FIG. 8A;

FIG. 9A is a cross-sectional view of a section of the device of FIG. 8A taken along lines 9A-9A;

FIG. 9B is a cross-sectional view of a section of the device of FIG. 8A taken along lines 9B-9B.

FIG. 10A is a front elevational view of an embodiment of a device;

FIG. 10B is a front elevational view of a section of the device of FIG. 10A;

FIG. 11 is a perspective view of an embodiment of a device;

FIG. 12A is a perspective view of an embodiment of a drive assembly;

FIG. 12B is a perspective view of an embodiment of a drive assembly;

FIG. 13 is a cross-sectional view of a section of the device of FIG. 11 taken along lines 13-13;

FIG. 14A is a perspective view of an embodiment of a drive assembly;

FIG. 14B is a perspective view of an embodiment of the drive assembly of FIG. 14A;

FIG. 17 is a front elevational view of an embodiment of a device; and

FIG. 18 is a front elevational view of an embodiment of a drive assembly.

DETAILED DESCRIPTION OF PREFERRED EMBODIMENTS

Figure 7A:
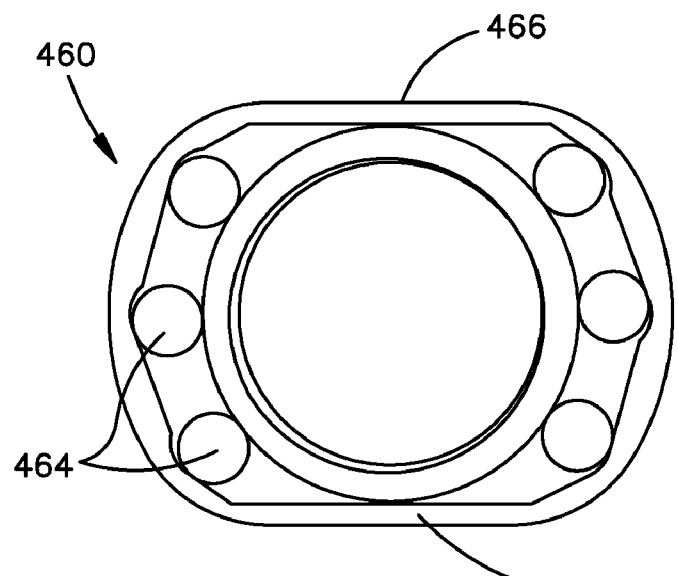
FIG. 7A is a side elevational view of an embodiment of a clutch mechanism.

Certain exemplary embodiments of the invention will now be described with reference to the drawings. In general, such embodiments relate to a device for displacing tissue within the body of an animal, by way of non-limiting example, a person with spinothoracic deformity. A child with spinothoracic deformity often requires an implant periodically adjusted to expand the ribcage to permit organs to freely grow thereunder without being crowded. Accordingly, it is desirable to provide a device in accordance with an embodiment of the invention which provides remote adjustment of such an implant. Remote adjustment refers to the ability to adjust the device without having to undergo surgery or other invasive or non-invasive procedure.

Reference is made generally to FIGS. 1-4, wherein an exemplary embodiment of a device for displacing tissue is shown. Device for displacing tissue 100 can be substantially straight, curved, or have another shape in accordance with design choice. One embodiment of device 100 may include a first member 120 and a second member 140 which are selectively displaceable with respect to each other, preferably telescopically displaceable. In the embodiment illustrated, device 100 includes a drive assembly 200, which displaces first member 120 from second member 140 to extend and/or retract device 100. Preferably, first member 120 includes a tubular member 122 having an inner cavity within which rod 142 of second member 140 may be received. It is to be understood that whereas certain embodiments are described herein as having a drive member associated with a tubular member, the drive member may be associated with a rod and vice versa.

First member 120 may include a first attaching device 124 for attaching to a tissue, for example bone within the body. Likewise, second member 140 may include a second attaching device 144 for attaching to a tissue within the body. The first and second attaching devices may be hooks, clamps, closed rings or other mechanisms that can attach to bone, for example, ribs. Examples of suitable clamps are described in U.S. Pat. No. 6,126,664 for "DEVICE AND METHOD FOR LOCATING AND RESECTING BONE;" U.S. Pat. No. 6,143,031 for "INTERVERTEBRAL IMPLANT WITH COMPRESSIBLE SHAPED HOLLOW ELEMENT;" U.S. Pat. No. 5,092,889 for "EXPANDABLE VERTICAL PROSTHETIC RIB;" U.S. Pat. No. 5,030,235 for "PROSTHETIC FIRST RIB;" and U.S. Pat. No. 5,261,908 for "EXPANDABLE VERTICAL PROSTHETIC RIB."

As device 100 is extended, first member 120 may be displaced from second member 140 and the respective tissues may be pushed away from each other. For example, if first member 120 is attached to a rib and second attaching device 140 is attached to the hip, the rib bone may be pushed outward to facilitate correcting a spinothoracic deformity.

In FIGS. 2-3, an exemplary embodiment of the drive assembly is shown, wherein a drive member 210 having an inner surface 216 and an outer perimeter 218 contacts tubular member 122 of first member 120. It is contemplated that drive member 210 may be connected to tubular member 122, for example, via a pivot between first attaching device 124 and tubular member 122. Drive member 210 is preferably generally cylindrical, such as a nut, has an inner surface 216 that is threaded, and further may include one or more teeth 212 along its outer perimeter 218. Preferably, as drive member 210 rotates, its inner surface 216 threadingly engages outer perimeter 146, preferably having a plurality of threads 148, of rod 142, and drive member 210 may thus move relative to, preferably along the length of, second member 140. Simultaneously, first member 120, which is preferably pushed by drive member 210, is also moved relative to, more preferably along the length of, second member 140. Furthermore, the inner surface 216 of drive member 210 and the outer perimeter 146 of rod 142 may cooperate to prevent slippage, and thus retain first member 120 and second member 140 in position. Whereas drive member 210 is shown as being contacting an end of tubular member 122, it is to be understood that drive member 210 may contact tubular member 122 at another location along the length thereof. Alternatively, drive member 210 may contact rod 142, wherein drive member 210 may threadingly engage an inner threaded surface of tubular member 122 to push rod 142.

The embodiments of drive assembly 200 includes a housing 220 having a first wing 230 and a second wing 232 which project outward from drive member 210, preferably at approximately 180 degrees from each other. Housing 220 preferably includes one or more projections, such as engagement teeth 222 to engage the one or more teeth 212 of drive member 210. Therefore, the rotation of housing 230 may result in the rotation of drive member 210. For example, in the embodiment shown in FIG. 3, by depressing first wing 230, drive member 210 may be rotated in a clockwise direction. However, because of the direction and arrangement of teeth 212 and engagement teeth 222, depressing second wing 232 does not rotate drive member 210. Rather, engagement teeth 222 of housing 220 slides over teeth 212, thus returning housing 220 to its position prior to having first wing 230 depressed. Therefore, a ratcheting effect may be provided. However, it is to be understood that housing 220 may be constructed and arranged to rotate drive member 210 in both directions without deviating from the scope of the invention, as a matter of design choice. Additionally, housing 220 may include one engagement tooth rather than a plurality of engagement teeth 222 as illustrated. Alternatively, housing 220 may include projections, detents, etc. to prevent the reverse rotation of drive member 210 without deviating from the scope of the invention.

Reference will now be made to FIGS. 4-6, wherein certain embodiments of the device include first member 340 displaceable relative to the length of second member 320 by a drive assembly 400 having a clutch mechanism such as a freewheel clutch 440, and a lever 430 for rotating freewheel clutch 440. In the embodiments shown, first member 340 includes a rod 342 having an outer perimeter 346 that preferably is at least partially threaded and second member 320 includes a tubular member 322 having an inner cavity 326 that is preferably substantially smooth. Drive assembly 400 includes a drive member 410 preferably having a generally cylindrical shape and an outer perimeter 414. Drive member 410 comprises an inner surface 416, at least a part of which is threaded to engage the outer perimeter 346 of rod 342 of first member 340, which is also at least partially threaded, thus permitting drive member 410 to move relative to the length of rod 342. Preferably, drive member 410 is concentrically aligned with rod 342.

Whereas a variety of drive assemblies may be used in accordance with the device, one embodiment of a suitable drive assembly 400 is shown in FIGS. 4-6. In the embodiment shown, drive assembly 400 includes a freewheel clutch 440 having one or more, preferably a plurality of, rollers 444, by way of non-limiting example, needles or rollers, surrounded by an outer housing 442 which is preferably aligned with, more preferably concentrically aligned with, drive member 410. In the embodiment of freewheel clutch 440 shown, outer housing 442 has inner walls 446 having an incline such that inner walls 446 include converging walls 446a.

An embodiment of drive assembly 400 as shown in FIGS. 4-6C includes a lever 430 extending radially outward from freewheel clutch 440 and peripherally fixed thereto. FIGS. 6A-C illustrate positions (1) thru (3) of freewheel clutch 440. As illustrated, lever 430 is preferably displaced by depressing a button 450 in direction A from a start position (1) to a depressed position (2) which in turn displaces lever 430 as illustrated. When button 450 is released, a spring 452 applies a force in direction B on button 450 to return button 450 to its start position (3). Preferably, the distance button 450 is displaced is limited by a housing 455, which encloses drive assembly 400. Therefore, the degree of rotation of drive member 410 may be controlled.

Preferably, as outer housing 442 rotates in a clockwise direction, rollers 444 are stopped and wedged between converging walls 446a and outer perimeter 414 of drive member 410. A clockwise torque is preferably generated, for example, by a frictional force evoked by the wedged roller 444. Therefore, the greater the torque generated, the more roller 444 may become wedged, thus increasing the frictional force between outer perimeter 414 of drive member 410 and rollers 444. Freewheel clutch 440 may also include one or more springs 448 which urge rollers 444 toward converging walls 446a.

Preferably, when button 450 moves in direction B, outer housing 442 rotates in a counter-clockwise direction and rollers 444 are permitted to roll away from converging walls 446a of outer housing 442. The work torque required to rotate drive member 410 in the opposite direction is preferably greater than the force necessary for rollers 444 to move or roll around the outer perimeter 414 of drive member 410. Therefore, outer housing 442 may rotate in a counter-clockwise direction without resulting in the rotation of drive member 410. Accordingly, drive assembly 400 preferably provides a ratcheting effect, by rotating drive member 410 in one direction and not the other, while lever 430 is displaced back and forth by displacing button 450 in directions A and B. Therefore, a ratcheting effect may be provided.

Therefore rollers 444 may roll away from converging walls 446a while drive member 410 remains in place. Whereas FIGS. 5-6 show nine rollers 444, it is to be understood that the number of rollers 444 may be varied as a matter of design choice and to fit the desired application. By way of non-limiting example, as shown in FIG. 7A, an alternate embodiment of freewheel clutch 460 includes six needles 464 and a housing 462 having a relatively elongated cross section. The elongated cross section may permit a narrower device. Moreover, in accordance with the embodiment of the freewheel clutch shown, outer housing 460 may have a partially flattened portion 466 which may provide a relatively low profile of device and reduce discomfort and cause less tissue irritation.

Figure 7B:
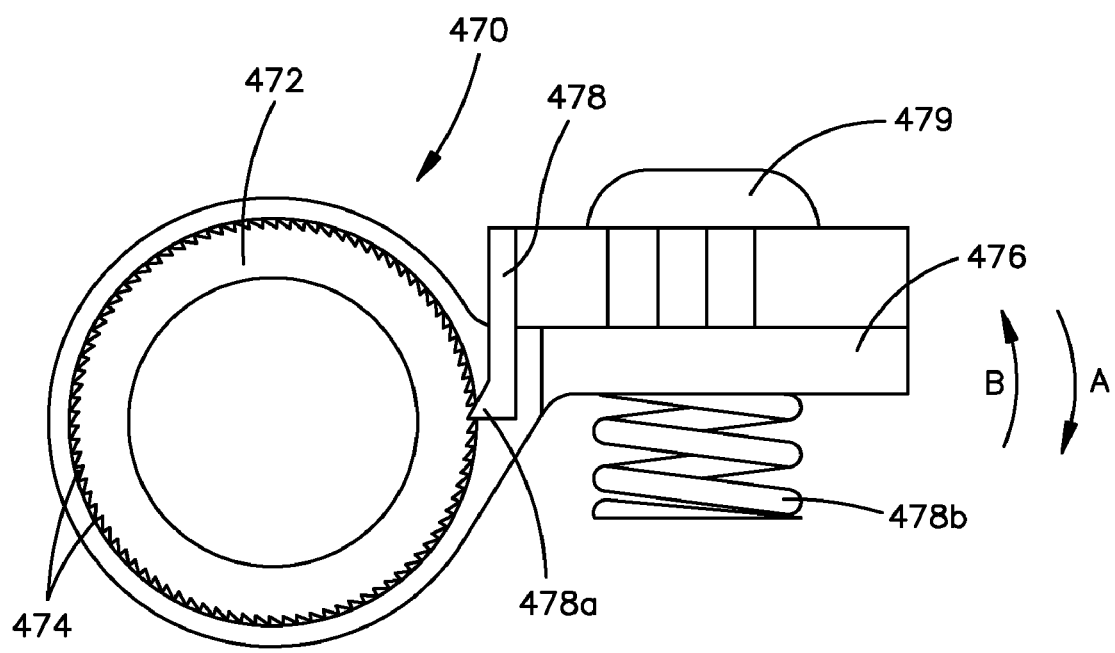
FIG. 7B is a side elevational view of an embodiment of a drive assembly.

In accordance with another embodiment of the drive assembly 470 as shown in FIG. 7B, drive assembly 470 may include a drive member 472 having a plurality of teeth 474 and grooves 475 within an outer housing 480, drive member 472 preferably being concentrically aligned with outer housing 480. Outer housing 480 is preferably associated with a lever 476 having a shaft 478 having a projection 478a constructed and arranged to be selectively received within grooves 475 of drive member 472.

As illustrated in FIG. 7B, as lever 476 is displaced in direction A, projection 478a of shaft 478 engages a groove 475 of drive member 472 and rotates drive member 472 in a clockwise direction. When lever 476 is displaced in direction B, however, because of the angle of teeth 474 and projection 478a of shaft 478, projection 478a of shaft 478 glides across teeth and thus drive member 472 does not rotate in the clockwise direction, thus creating a ratcheting effect. Lever 476 may be displaced by depressing a button 479 in direction A. Preferably, a spring 478b applies a force in direction B on button 479, thus returning button 479 to the start position in accordance with the embodiment described above.

Whereas an embodiment of drive assembly 400 having a lever 430 has been illustrated herein as rotating drive member 410 along rod 342 of first member 320, it is to be understood that drive member 410 may be rotated within tubular member 322 of second member 320 without deviating from the scope of the invention. Alternate embodiments are also contemplated.

Referring to FIGS. 8A-9B, an embodiment of device 500 may include a rod 502 and a tubular member 522 which are displaceable relative to each other. Device 500 may have a curvature, and more preferably has a radius of curvature of about 220 mm. Such curvature may be beneficial for use with a spine, for example, within a chest wall. Additionally, device 500 may be constructed to substantially minimize tissue resistance, for example, when device 500 is being extended. Referring to FIG. 8A, tubular member 522 may include a relatively sharp edge 523 which preferably cuts through the tissue within a patient's body as device 500 is being extended. When a portion 530 of tubular member 522 projects away from rod 502 thus potentially increasing resistance as device 500 extends sharp edge 523 may be additionally helpful to cut through the tissue. Portion 530 may be utilized for a variety of functions, for example, for housing a lever, gears, a button and the like.

In accordance with a preferred embodiment of rod 502 as shown in FIGS. 8A and 9A-B, rod 502 includes a generally cross-shaped or (X shape) cross section, four sides 504a,b, 506a,b and has at least a partially threaded portion 508. As shown, rod 502 can include two threaded sides 504a,b having a first radius of curvature, and two smooth sides 506a,b having a second radius of curvature preferably different from the first curvature, wherein threaded sides 504a,b and smooth sides 506a,b are alternatingly positioned around the perimeter of rod 502.

Preferably, drive member 510 includes a threaded portion 512 which may engage threaded sides 504 to move relative to the length of rod 502 as well as remain in place without slipping. Smooth sides 506 preferably do not contact drive member 510 and therefore do not create interference against drive member 510. More preferably, smooth sides 506a,b have a smaller diameter than threaded sides 504a,b, thus facilitating not contacting drive member 510.

Additionally, referring to the embodiment shown in FIG. 9A, device 500 may have a top 503a and a bottom 503b, wherein device 500 curves from top 503a toward bottom 503b. Threaded sides 504a,b may be proximate the sides 503c of device 500. Preferably, threaded sides 504a,b are not proximate top 503a where the distance between the threads may increase or the threads become wider because of the curvature of rod 502. Threaded sides 504a,b are preferably not proximate bottom 503b of device 500 either, where either the distance between the threads may decrease or the threads become narrower because of the curvature of rod 502, thus potentially creating clumping of threads. Furthermore, providing a smaller diameter of smooth sides 506a,b may prevent jamming the bottom of drive member 510. It is to be understood that rod 502 may include more or less threaded sides 504a,b or smooth sides 506a,b, and the positioning of threaded sides 504a,b and smooth sides 506a,b on rod 502 may be altered as a matter of design choice.

Referring to FIGS. 8A and 9A, tubular member 522 may include a slot generally indicated at 524 through which rod 502 may be seen and accessed. This embodiment of device 500 may facilitate manufacture by providing slot 524 for access by a machine tool while maintaining device 500 relatively compact.

FIG. 9B illustrates a cross section of an exemplary embodiment of drive member 510 positioned along the length of rod 502, the cross section take along line C-C of FIG. 8A. Drive member 510 preferably comprises a generally cylindrical shape and a threaded portion 512 proximate the middle region of drive member 510 to engage threaded sides 504 of rod 502 preferably with non threaded regions proximate both end portions 526. Drive member may be operably associated with a rotating mechanism, such as a freewheel clutch 511 for rotating drive member 510. Preferably, threaded portion 524 is approximately 4 mm long, and end portions 526 of drive member 510 do not include threads. There is preferably no interference between end portions 526 and rod 502, which may facilitate the rotation of drive member 510 along rod 502 having a curvature.

Referring to FIG. 10A, a device 550 may include two or more first members 560 having rods 562, two or more second members 570 having tubular members 572, two or more drive members 580 associated with, preferably fixed to rods 562 and located within tubular members 572, and an actuator 590. It is to be understood, however, that the drive members can be fixed to tubular members 572 and movable relative to rods 562. Rods 562 and tubular members 572 may be relatively curved or straight, more preferably straight. In accordance with a preferred embodiment, device 550 may include two relatively straight first members 560 positioned at an angle with respect to each other. Therefore, device 550 may better fit the body of the patient while facilitating manufacture.

In the embodiment shown, actuator 590 is associated with rods 562 such that the activation of actuator 590, for example, the rotation of a freewheel clutch, results in the rotation of rods 562, preferably simultaneously. Actuator 590 is preferably associated with rods 562 via a flexible coupling 592, such as a cardan coupling or universal joint. Drive member 580 may be associated with, preferably fixed to, rods 562, such that the rotation of rods 562 rotates drive members 580. Actuator 590 is preferably activated by a button, lever, etc. that may be depressed, more preferably a button that may be depressed from outside the body of the patient.

Preferably, drive member 580 is located within tubular member 572. Tubular member 572 preferably includes an inner cavity 574 having a threaded region 576. Drive member 580 preferably includes a plurality of threads 582 on its outer perimeter 584, thus engaging threaded region 576 of tubular members 572 to move drive members 580 relative to the length of tubular members 572.

Second members 570 may include an attaching element 578 to attach to tissue in the body of an animal and a tubular member 572. Therefore, as first members 560 are displaced relative to the length of second members 570, device 550 may be extended or retracted accordingly, thus moving the tissues of the body closer together or further apart. Such an arrangement may facilitate manufacturing device 550, and may be beneficial by partially straightening out as device 550 is extended, especially in patients where a device having a fixed curvature may lead to a too strong kyphosis when fully expanded. Furthermore, actuator 590 preferably remains fixed within the patient's body regardless of how much device 550 is extended or retracted.

In accordance with the embodiment shown in FIG. 10A, first members 560 include housings 568 for enclosing rods 562. Housings 568 may include grooves 569, preferably running externally along the length of housing 568. Tubular members 572 may include projections or pins 576 projecting toward housings 568. Pins 576 are preferably constructed and arranged to be received within groove 564 to substantially prevent the rotation of tubular member 572 with respect to housing 568 and vice versa, thus substantially preventing device 550 from rotating within the patient's body.

Reference is now made to FIGS. 11-13, wherein an exemplary embodiment of device 600 is illustrated as having a first member 620 telescopically displaceable from a second member 640, wherein second member 640 includes a drive assembly 700 having a pushbutton 720 that may be depressed. More specifically, to obtain distraction or retraction a user may operate and move pushbutton 720 manually from outside the skin by applying pressure to the patient's skin. In the embodiment shown, pushbutton 720 includes a spring 722 on its underside having a fixed first end 724 attached to second member 620 via a bolt 725. Spring 722 may also include a free second end 726 that is displaceable as pushbutton 720 is depressed and released. By way of non-limiting example, when pushbutton 720 is depressed, second end 726 engages a tooth 732 of a toothed wheel 730, and when pushbutton 720 is depressed, the free end 726 moves away from fixed end 724 thus rotating toothed wheel 730. When pushbutton 720 is released, second end 726 slides above the surface of teeth 732 of toothed wheel 730 back to its starting position, without rotating toothed wheel 730. Additionally, the biasing force applied by spring 722 on tooth 732 of toothed wheel 730 substantially prevents the reverse rotation of toothed wheel 730.

When toothed wheel 730 is rotated by depressing pushbutton 720, a threaded bolt 740 is also rotated. Threaded bolt 740 may be either integral to or cooperatively attached to toothed wheel 730 as a matter of design choice. Threaded bolt 740 preferably rotates and engages a threaded worm gear 750, thus rotating worm gear 750. Worm gear 750 may be connected to a spindle 760, which is activated by the rotation of worm gear 750. Spindle 760 may include a threaded surface 762, which engages a drive member 710. Drive member 710 preferably is generally cylindrial and has at least a portion of an inner surface 712 which is threaded. The rotation of drive member 710 preferably results in the movement of drive member 710 along spindle 760, which in turn, results in first member 620 being displaced along the length of second member 640. Therefore, by depressing pushbutton 720, device 600 may be extended. Device 600 may also be configured to retract upon depressing pushbutton 720.

Figure 15:
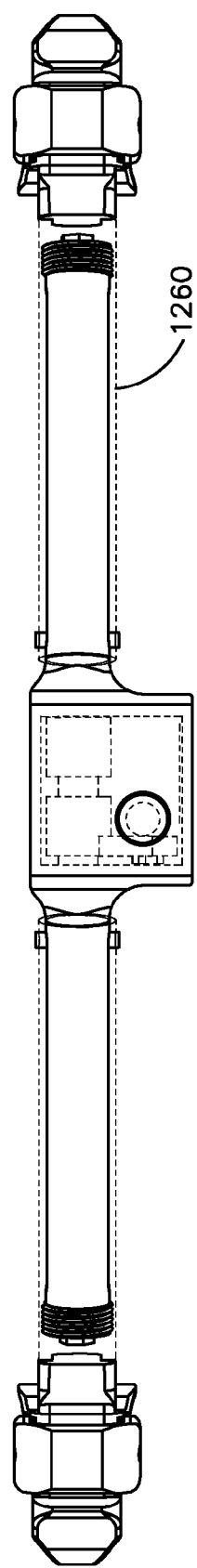
FIG. 15 is a top planar view of an embodiment of a device.

In FIGS. 14A-B, an alternate embodiment of device 600 is illustrated having two pushbuttons. Pushbutton 720 may be depressed to extend device 600 as described above. Additionally, a second pushbutton 770 may be provided to either further extend device 600 or alternatively, to retract device 600 when second pushbutton 770 is depressed. Preferably, second pushbutton 770 includes a second spring having an end that contacts and pushes a tooth of toothed wheel 730 to rotate toothed wheel 730. By way of non-limiting example, pushbutton 720 may be constructed and arranged to rotate toothed wheel 730 in a first direction when pushbutton 720 is depressed. Preferably, second pushbutton 770 is also constructed and arranged to rotate toothed wheel 730 in the first direction when second pushbutton 770 is depressed. For example, each pushbutton 720 and second pushbutton 770 may rotate toothed wheel 730 by approximately half a tooth. Therefore, by alternating depressing pushbutton 720 and second pushbutton 770, toothed wheel 730 may be rotated approximately one tooth. Alternatively, second pushbutton 770 may be constructed and arranged to rotate toothed wheel 730 in a second direction different to the first direction in either the first direction FIG. 15 illustrate an embodiment of device 650 having a first freewheel clutch 680 for rotating two or more rods 662 in a first direction, and a second freewheel clutch 682 to prevent rods 662 from rotating in a second direction opposite to the first direction. Preferably, first freewheel clutch 680 is associated with a pushbutton 690, and second freewheel clutch 682 is associated with, preferably fixed to, a housing 684 substantially enclosing second freewheel clutch 682. Device 650 as described may be beneficial in situations when each rotation of first freewheel clutch 682 is insufficient to transfer enough torque to rotate one or more drive members 690. In such a situation, rods 662 may oscillate back and forth without rotating drive members 690. Second freewheel clutch 682 may at least substantially prevent the oscillation of rods 662 by preventing the reverse rotation of rods 662.

Figure 16A:
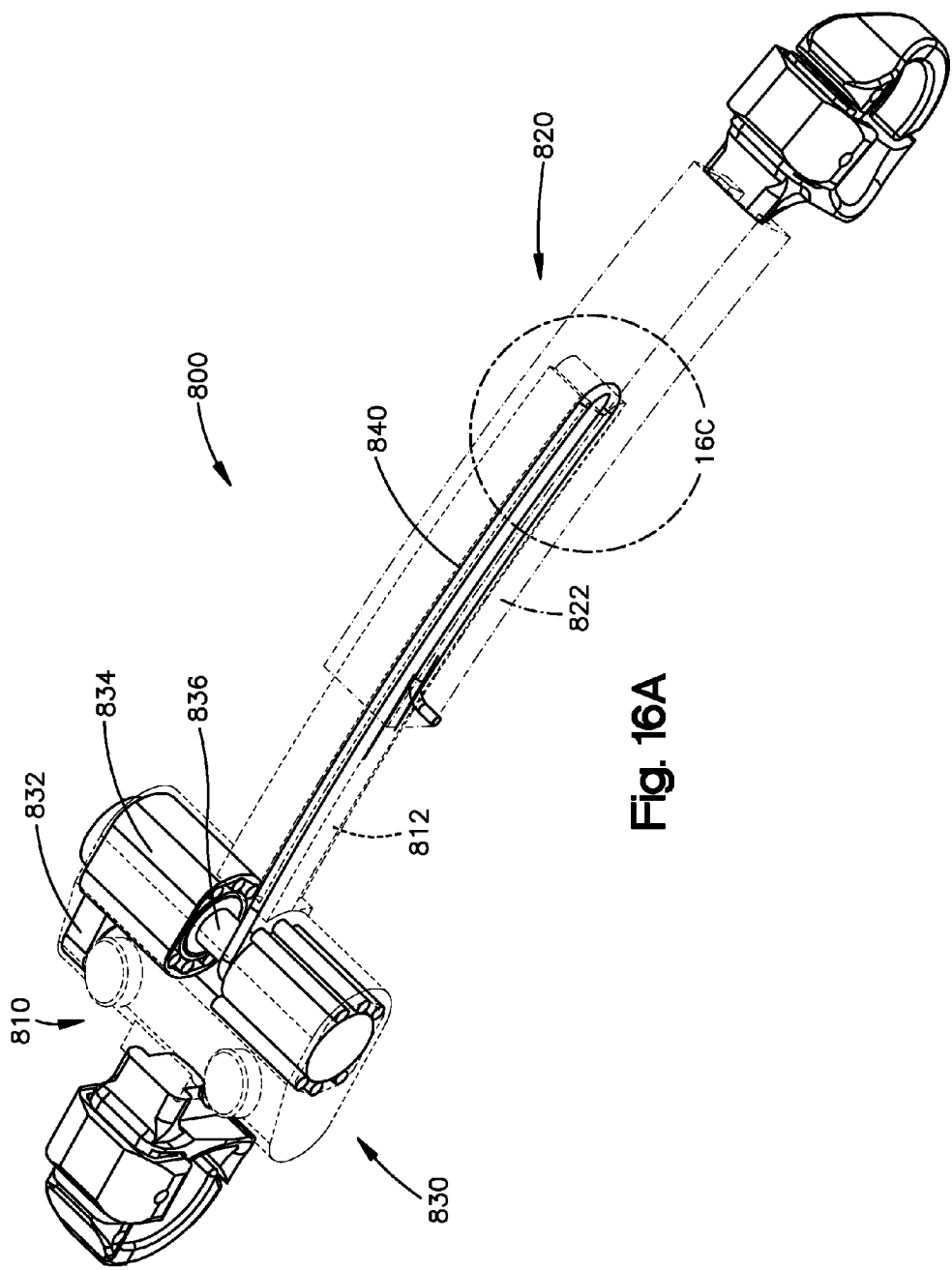
FIG. 16A is a perspective view of an embodiment of a device.
Figure 16B:
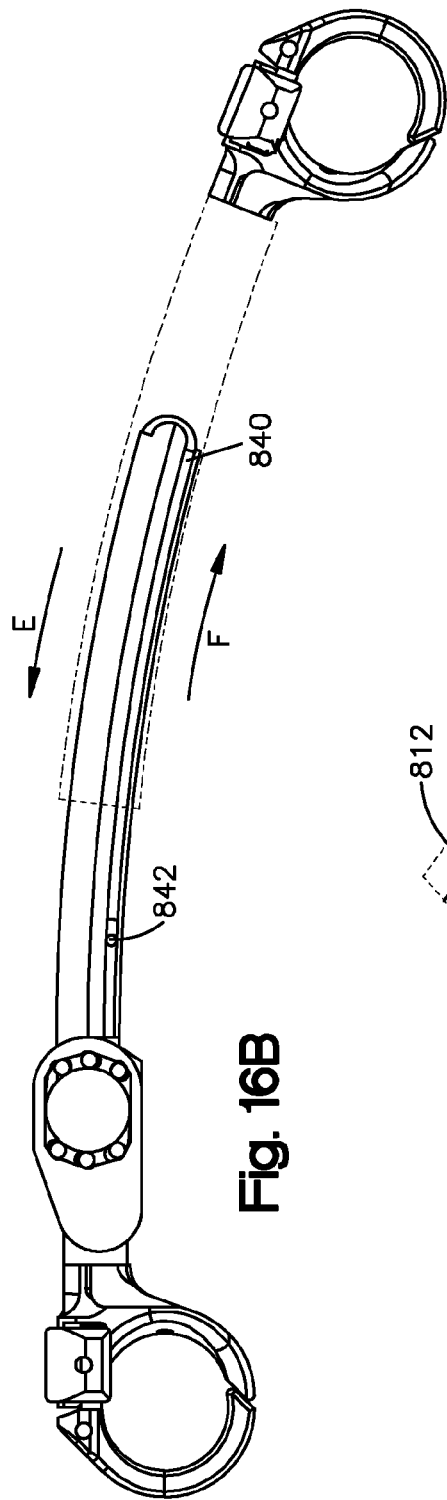
FIG. 16B is a front elevational view of the device of FIG. 16A.
Figure 16C:
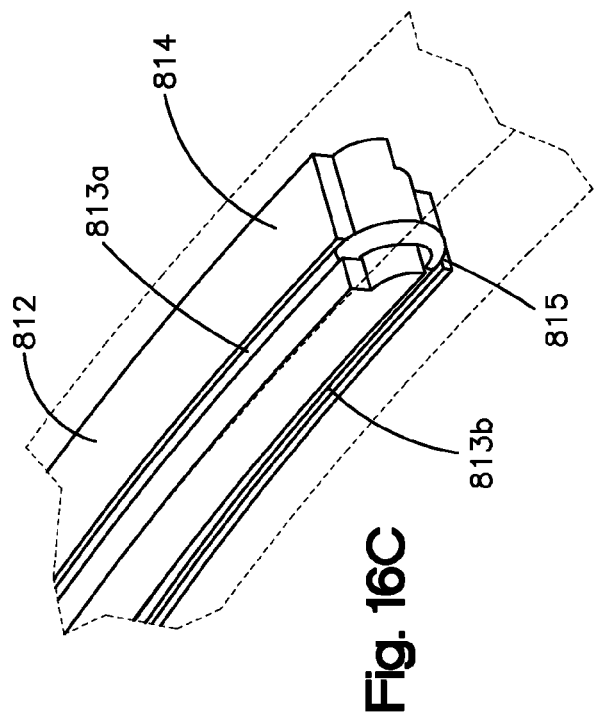
FIG. 16C is a perspective view of a section of the device of FIG. 16.

Reference is now made to FIGS. 16A-C, wherein an embodiment of device 800 is illustrated having a first member 810 having a rod 812 and a second member 820 having a tubular member 822, further including a drive assembly 830 associated with rod 812 for selectively displacing first member 810 with respect to second member 820. More specifically, drive assembly 830 may include an actuator 832 for activating a first freewheel clutch 834 which preferably rotates a shaft 836 which winds a cable 840 preferably about shaft 836. In the embodiment shown, cable 840 is received within a channel 813a which runs along the length of rod 812 on a first side 814 and a channel 813b which runs along the length of rod 812 on a second side 815 such that when cable 840 is being wound about shaft 836, cable 840 moves in a first direction D in channel 813a and in a second direction E, preferably different from first direction D, in channel 813b. Whereas FIG. 16 illustrate an embodiment of device 800 wherein first side 814 is different from second side 815, it is to be understood that first side 814 and second side 815 may be the same side as a matter of design choice. Preferably, a first end 842 of cable 840 is connected, more preferably fixed, to tubular member 822. Therefore, as first freewheel clutch 834 is rotated, cable 840 is wound about shaft 836 and first end 842 of cable 840 is pulled in direction E, thus displacing tubular member 822 in direction E, away from drive assembly 830 and thus extending device 800.

One preferred embodiment of the device has a length of about 10 to 200 mm, more preferably about 20 to 180, most preferably about 30 to 150 mm when fully contracted. Additionally, one embodiment of the device has a length of about 20 to 400 mm, more preferably about 30 to 350 mm, most preferably about 40 to 300 mm when fully extended. The radius of curvature of the device is preferably between about 100 and 300 mm, more preferably between about 150 and 250 mm, most preferably about 220 mm. However, it is to be understood that the preferred shape, length, curvature, and the like, of the device varies according to the body in which the device is to be inserted, preferably implanted.

Whereas various embodiments of the drive assembly having a lever 430 has been illustrated herein as rotating a threaded member along a rod, it is to be understood that the threaded member may be rotated within the tubular member, or an alternate arrangement may be provided without deviating from the scope of the invention. Likewise, it is to be understood that a device be generally straight or curved without deviating from the scope of the invention.

Additionally, whereas certain embodiments of the driving member are described herein as having external threading, one of ordinary skill in the art would appreciate that the embodiments of the drive member may have internal threading, and vice versa, as a matter of design choice. For example, providing internal threading may provide an increased driving force.

Shape Memory Allow Drive Assembly

An adjustable device for displacing tissues within a body may include a drive assembly for extending and/or retracting the device comprising a shape memory alloy. In accordance with an embodiment shown in FIGS. 17-18, a device 900 includes a first member 920 and a second member 940 selectively displaceable with respect to each other. Referring to the embodiment shown, drive assembly 950 includes a heat element 952, preferably a conductive material such as copper. Preferably, heat element 952 may be heated by induction of an electrical current through the skin. When heated, heat element 952 may contract an actuator 955, which preferably comprises a shape memory alloy, Nitinol. The contraction of actuator 955 displaces a clapper 956 toward actuator 955 in direction C.

First member 920 as shown includes a plurality of teeth 922, which clapper 956 may engage. In the embodiment shown, as clapper 956 is displaced toward direction C, clapper 956 pushes first member 920 in direction C to extend device 900. Preferably, clapper 956 is displaced at least the length of one tooth 922. In accordance with a preferred embodiment of the invention, the length of one tooth 922 is approximately 0.75 mm. Therefore, each time actuator 955 is activated, device 900 may be extended approximately 0.75 mm.

In the embodiment shown in FIGS. 17-18, a retaining spring 958 is not affected by the contraction of actuator 955. Rather, as clapper 956 displaces first member 920 the length of one tooth 922 in direction C, retaining spring 958 glides over tooth 922 to engage the adjacent tooth in direction D. Once actuator 955 cools by heat dissipation, a set back spring 954 of actuator 955 may deform to its length at least substantially equal to its length prior to heat element 952 being heated. Actuator 955 thus extends and clapper 956 is displaced in direction D. Preferably, clapper 956 pivots as it moves in direction D. As shown, clapper 956 does not pivot in the opposite direction because of the shape and arrangement of clapper 956 and teeth 922. As clapper 956 is displaced in direction D, first member 920 remains in place because of the engagement of retaining spring 958 and teeth 922. Accordingly, the distance between clapper 956 and retaining spring 958 returns to its original distance prior to heating heat element 952, thus resetting driving assembly 950 for the next activation.

It is to be understood that in accordance with an embodiment of the device, the first and second members can be constructed and arranged such that as the device extends and contracts, a part of the first member may move along the side of a part of the second member, such as for example adjacent rods.

Whereas many embodiments were described independently, it is to be understood that the various features of the different embodiments may be combined, altered, etc. as a matter of design choice.

Although the present invention and its advantages have been described in detail, it should be understood that various changes, substitutions, and alterations may be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art.

We claim:

1. An expandable device for moving tissue, the device comprising:
    a first elongated member having a threaded portion;
    a second elongated member operably associated with a driving member, the driving member having a threaded portion constructed and arranged to engage the threaded portion of the first elongated member;
    a displacement mechanism including a lever; and
    a clutch mechanism associated with the displacement mechanism, wherein the lever extends laterally away from an outer surface of the clutch mechanism, and the driving member, the clutch mechanism having a first condition wherein upon movement of the lever for rotation of the displacement mechanism in a first direction, the driving member rotates in the first direction, the clutch mechanism having a second condition wherein upon movement of the lever for rotation of the displacement mechanism in a second direction different from the first direction, the driving member remains stationary without rotating.

2. The expandable device of claim 1, further comprising at least one first tooth associated with the displacement mechanism and at least one second tooth associated with the driving member, wherein at least one of the first engagement tooth selectively engages at least one of the second tooth upon rotation of the displacement mechanism in the first direction such that the driving member rotates as the clutch displacement rotates.

3. The expandable device of claim 1, wherein the clutch mechanism comprises an intermediate member positioned between the driving member and the displacement mechanism, the intermediate member comprising at least one first tooth; wherein the driving member includes at least one second tooth.

4. The expandable device of claim 1, wherein the clutch mechanism comprises an intermediate member positioned between the driving member and the displacement mechanism, the intermediate member comprising at least one first tooth; wherein the displacement mechanism includes at least one second tooth.

5. The expandable device of claim 4, wherein the intermediate member is fixed with respect to the displacement mechanism.

6. The expandable device of claim 4, wherein the first elongated member includes a first attachment mechanism and the second elongated member includes a second attachment mechanism, wherein the first attachment mechanism and the second attachment mechanism are constructed and arranged to attach to a tissue.

7. A bone displacement apparatus comprising:
    a first attachment member;
    a second attachment member;
    a driven member coupled to the first bone attachment member;
    a rotatable driving member coupled to the second bone attachment member;
    screw threads engaged between the driving member and the driven member to move the driven member axially relative to the second bone attachment member for displacement of the bone attachment members upon rotation of the driving member in a displacement direction;

a manually rotatable actuator including a lever laterally extending away from an outside surface of the clutch mechanism; and a clutch mechanism operative between the actuator and the driving member to advance the driving member in the displacement direction upon rotation of the actuator back and forth in opposite directions using the lever, the clutch being interposed radially between the actuator and the driving member in a position axially overlying the screw threads positioned between the driving member and the driven member.

8. The apparatus of claim 7 wherein the screw threads are oriented to move the driven member axially apart from the second bone attachment member for distraction of the bone attachment members upon rotation of the driving member in the displacement direction.

9. The apparatus of claim 7 wherein the driving member is rotatable in opposite directions relative to the first and second bone attachment members.

10. A bone displacement apparatus comprising:
a first bone attachment member;
a second bone attachment member having a driving member;
an actuator;
a clutch mechanism operatively associated with the driving member to advance the driving member in a displacement direction, the clutch mechanism including
a plurality of rollers;
a housing containing the rollers and the driving member, the housing having a converging inner wall portion;
a first condition wherein upon rotation of the housing in a first direction, the rollers are wedged between the housing and the driving member, and the driving member rotates in the first direction; and
a second condition wherein upon rotation of the housing in a second direction different from the first direction, the driving member remains stationary without rotating;
wherein the actuator includes a displaceable lever, the lever constructed and arranged to rotate the housing in the first direction upon displacement of the lever in a first displacement direction, the lever further constructed and arranged to rotate the housing in the second direction upon displacement of the lever in a second displacement direction.

11. The apparatus of claim 10, further comprising a pushbutton operatively associated with the lever such that upon depression of the pushbutton, the lever is moved in the first displacement direction.

12. The apparatus of claim 10, further comprising a spring constructed and arranged to urge the lever in the second displacement direction.

13. The apparatus of claim 10, wherein the first and second bone attachment members include an attachment mechanism for attaching to a bone.

14. The apparatus of claim 10, further comprising screw threads engaged between the driving member and the second bone attachment member to move the first bone attachment member axially relative to the second bone attachment member upon rotation of the driving member in a displacement direction.

15. The apparatus of claim 10, wherein the driving member is rotatable in a first direction to displace the first attachment member away from the second attachment member, the apparatus further comprising a second clutch mechanism constructed and arranged to prevent the driving member from advancing in a second direction different from the displacement direction.

16. The apparatus of claim 10, wherein at least one of the bone attachment devices includes a slot.

17. The apparatus of claim 10, wherein the actuator includes a gear train.

18. The apparatus of claim 10, wherein the actuator is adjacent to the driving member.

19. The apparatus of claim 10, further comprising a cable having a first end coupled to a shaft and a second end coupled to the first bone attachment member, wherein the shaft is connected to the clutch mechanism, the clutch mechanism being configured to rotate the shaft to displace the first attachment member from the second attachment member.

20. The apparatus of claim 10, further comprising two intermediary members between the first and second attachment members, wherein the actuator is positioned between the two intermediary members.

21. The apparatus of claim 10, further comprising a projection connected to the second attachment member and wherein the first attachment member includes a groove for receiving the projection.

22. The apparatus of claim 10, further comprising a radius of curvature of about 220-240 mm.

23. The apparatus of claim 10, wherein the first bone attachment member has a portion having a generally cross-shaped cross-section, the portion including:
a threaded portion having a first threaded side constructed and arranged to engage the driving member; and
a second side that does not engage the driving member.

24. The apparatus of claim 23, wherein the portion includes two first threaded sides and two second sides.

25. The apparatus of claim 23, wherein the first threaded side has a first length and the second side has a second length less than the first length.

26. The apparatus of claim 23, wherein the driving member includes a first end portion and a second end portion and a middle portion, wherein the middle portion includes a threaded region and the end portions do not have threading.

27. The apparatus of claim 10, further comprising a housing having a relatively sharp edge configured to displace tissue as the apparatus expands.

28. The apparatus of claim 10, wherein the driving member includes a threaded portion and an unthreaded end portion.

* * * * *